United States Patent
Sherman

(10) Patent No.: US 6,633,778 B2
(45) Date of Patent: Oct. 14, 2003

(54) HIGH-ENERGY, HIGH-FREQUENCY PULSE DEFIBRILLATOR

(75) Inventor: Marshall L. Sherman, Cardiff, CA (US)

(73) Assignee: Cardiac Pacemakers, inc., St. Paul, MN (US)

(*) Notice: Subject to any disclaimer, the term of this patent is extended or adjusted under 35 U.S.C. 154(b) by 335 days.

(21) Appl. No.: 09/745,282

(22) Filed: Dec. 20, 2000

(65) Prior Publication Data

US 2002/0077666 A1 Jun. 20, 2002

(51) Int. Cl.$^7$ ................................................. A61N 1/40
(52) U.S. Cl. ............................................................ 607/5
(58) Field of Search ................................ 607/4, 5, 6, 7, 607/8

(56) References Cited

U.S. PATENT DOCUMENTS

| | | | |
|---|---|---|---|
| 4,023,573 A | 5/1977 | Pantridge et al. | |
| 5,184,616 A | 2/1993 | Weiss | |
| 5,391,186 A * | 2/1995 | Kroll et al. | 607/5 |
| 5,522,850 A | 6/1996 | Yomtov et al. | |
| 5,531,768 A | 7/1996 | Alferness | |
| 5,534,015 A | 7/1996 | Kroll et al. | |
| 5,601,608 A | 2/1997 | Mouchawar | |
| 5,792,189 A | 8/1998 | Gray et al. | |
| 5,855,592 A | 1/1999 | McGee et al. | |
| 5,865,787 A * | 2/1999 | Shapland et al. | 604/21 |
| 5,928,278 A | 7/1999 | Kitschmann | |
| 6,298,266 B1 * | 10/2001 | Rubin et al. | 607/5 |

FOREIGN PATENT DOCUMENTS

| FR | 2 798 859 A1 | 3/2001 |
|---|---|---|
| WO | WO 01/21255 A1 | 3/2001 |

OTHER PUBLICATIONS

Beck et al., "Ventricular Fibrillation of Long Duration Abolished by Electric Shock," J.A.M.A., vol. 135, No. 15, Dec. 13, 1947, pp. 985–986.

Schuder et al., "Transthoracic Ventricular Defibrillation with Square–wave Stimuli: One–Half Cycle, One Cycle, and Multicycle Waveforms," Circulation Research, vol. XV, Sep. 1964, pp. 258–264.

Zoll et al., "Termination of Ventricular Fibrillation in Man by Externally Applied Electric Countershock," The New England Journal of Medicine, vol. 254, No. 16, Apr. 19, 1956, pp. 727–732.

Schuder et al., "Transthoracic Ventricular Defibrillation with Triangular and Trapezoidal Waveforms," Circulation Research, vol. XIX, Oct. 1966, pp. 689–694.

* cited by examiner

Primary Examiner—Sang Paik
(74) Attorney, Agent, or Firm—Fulwider Patton Lee & Utecht, LLP

(57) ABSTRACT

A pulse having a high-frequency cyclic waveform with a plurality of cycle groups is applied across a defribrillating heart. The waveform has, during the first cycle group, an initial peak-to-peak voltage and, during each subsequent cycle group, a peak-to-peak voltage that may be substantially equal to or less than that of the previous cycle group. In one application, the subsequent cycle groups have progressively decreasing peak-to-peak voltages and the profile of the cyclic waveform resembles a discharge curve of a capacitor. In another the subsequent cycle groups have substantially equal peak-to-peak voltages and the cyclic waveform has a substantially constant peak-to-peak amplitude throughout the duration of the pulse. The waveform of the pulse has substantially no dc component. The total energy delivered to the heart is controlled by adjusting the initial and subsequent peak-to-peak voltages and by varying the time duration of the pulse.

39 Claims, 3 Drawing Sheets

PRIOR-ART

PRIOR-ART

HIGH-ENERGY, HIGH-FREQUENCY PULSE DEFIBRILLATOR

BACKGROUND OF THE INVENTION

The invention relates generally to an apparatus and a method for treating cardiac arrhythmia or fibrillation, and more particularly, to a defibrillator system that employs high-frequency, high-energy pulses to correct arrhythmia or fibrillation.

Throughout this specification, the term "pulse" is used to describe a signal having an on duration during which a waveform having an appreciable voltage level is present. The waveform defining the pulse may be a dc waveform, e. g., a discharge curve of a capacitor, or a symmetric waveform, e. g., a sine wave.

Electrical energy is applied to patients for many reasons, two of which are to ablate cardiac tissue and to defibrilate the heart. In ablation, energy is applied to cause targeted tissue to increase in temperature until the tissue is no longer viable. This approach is taken in terminating arrhythmias of the heart. It has been found that applying ablation energy having a substantial dc component can cause the heart to fibrillate.

As is known to those skilled in the art, "fibrillation" is a condition in which individual muscle fibers quiver or spontaneously contract. In an atrium of the heart, it is indicated by extremely rapid, incomplete contractions of the atria resulting in fine, rapid, irregular, and uncoordinated movements. In a ventricle, it is a condition resulting in rapid, tremulous, and ineffectual contractions of the ventricles. In both cases, the heart is unable to pump necessary amounts of blood to sustain the patient. Fibrillation is to be avoided and thus, avoiding the application of energy with a substantial dc component to a non-fibrillating heart is recommended.

Defibrillator systems deliver a high voltage electrical counter shock to the heart in an attempt to correct or convert a detected cardiac arrhythmia or fibrillation. The typical defibrillator system includes a capacitor system that produces a pulse defined by a trapezoidal or exponential decay waveform. This pulse is delivered to the heart through electrodes. It is hoped that such a counter shock will allow the heart's normal pacemaker to take over.

A defibrillator system may be an external or internal device. An external defibrillator system applies energy to a patient through electrode pads. In an external defibrillator, a shock wave of approximately 200–400 joules is discharged across the chest through a pair of electrode pads positioned on the chest. An internal defibrillator system applies energy through an implanted device that includes a capacitor having leads terminating in the heart. In an internal defibrillator, a shock wave of approximately 40–80 joules is discharged through the heart.

In a typical defibrillator system, the pulses applied to the heart may be in the form of a monophasic or a biphasic pulse. As shown in FIG. 1, monophasic pulses comprise a single monotonically decaying electrical waveform that is typically truncated before the defibrillator capacitor system is completely discharged. The monophasic pulse comprises a substantial dc component. As shown in FIG. 2, a biphasic pulse comprises a pair of decaying electrical waveforms or phases that are of opposite polarity. As indicated in FIG. 2, the biphasic waveform is a non-recurrent, asymmetric waveform having unequal positive and negative portions. Accordingly, the biphasic pulse retains a substantial dc component. To generate a biphasic pulse, a first pulse or phase is discharged from a capacitor system in the same manner as a monophasic pulse and, at the point the first pulse is truncated, a switch circuit connected to the electrodes is used to immediately reverse the discharge polarity of the capacitor system as seen by the electrodes in order to produce the second waveform or phase of the biphasic pulse that is of the opposite polarity.

For either the monophasic or biphasic pulses, the pulse applied to the heart has a substantial dc component. However, it has been found that the application of dc current through the heart causes significant pain to the patient undergoing defibrillation. Therefore, it would be beneficial to a patient if a defibrillation pulse did not contain any appreciable dc component, yet still included enough energy to defibrilate the heart.

Hence, those skilled in the art have recognized a need for a defibrillator system that corrects or converts a detected cardiac arrhythmia or fibrillation in a way less painful than currently available defibrillator systems. The invention fulfills these needs and others.

SUMMARY OF THE INVENTION

Briefly, and in general terms, the invention is directed to an apparatus and a method for correcting or converting a detected cardiac arrhythmia or fibrillation.

In a first aspect, the invention is related to a method of applying energy to a heart, including defribrilating a heart that is in fibrillation. The method includes the step of applying, across the heart, a pulse comprising a high-frequency cyclic waveform having a plurality of cycle groups. The waveform has, during the first cycle group, an initial peak-to-peak voltage sufficient to shock the heart and, during each subsequent cycle group, a subsequent peak-to-peak voltage, the pulse substantially lacking a dc component. The method further includes the step of controlling the total energy delivered to the heart.

In a more detailed aspect of the method, each cycle group comprises at least one cycle of the cyclic waveform. In another aspect, each cycle group has a peak-to-peak voltage less than that of the previous cycle group. In yet another facet, the profile of the cyclic waveform resembles a discharge curve of a capacitor. In another, the initial peak-to-peak voltage of the cyclic waveform and each subsequent peak-to-peak voltage are substantially equal. In further aspects, when the pulse is applied external to the heart, the initial peak-to-peak voltage is between approximately 9000 volts and 10,000 volts and, when the pulse is applied internal to the heart, the initial peak-to-peak voltage is between approximately 1000 volts and 1200 volts. In still other aspects, the total energy is controlled by varying the peak-to-peak voltages and/or by varying the time duration of pulse.

In second aspect, the invention is related to a method of applying a high-energy, high-frequency pulse across a heart for restoring effective cardiac rhythm. The method includes the steps of charging a capacitor having a first terminal and a second terminal to an initial voltage level sufficient to shock the heart, applying the potential at the first terminal of the capacitor to a first cardiac-tissue contact point and applying the potential at the second terminal of the capacitor to a second cardiac-tissue contact point. The method further includes the steps of initiating the discharge of the capacitor and periodically interchanging the potentials at the first and second terminals of the capacitor during discharge of the capacitor to produce a waveform comprising a plurality of cycles each having a positive portion and a negative portion, the waveform substantially lacking a dc component.

In a detailed aspect of the method, the potentials are interchanged at fixed time intervals such that the cycles of the waveform have positive and negative portions of substantially equal time duration. In another aspect of the method, the potentials are interchanged until the capacitor is completely discharged. In another detailed facet of the method, the potentials are interchanged such that the cumulative energy of the positive portions is substantially equal to the cumulative energy of the negative portions. In another aspect, the potentials are interchanged such that, for each cycle, the energy in the positive portion is substantially equal to the energy in the negative portion. In a further aspect, the time duration of one portion of each cycle is greater than the time duration of the other portion of the same cycle. In still another facet, for each cycle, except the last, the potentials are interchanged such that the time duration of the positive portion is substantially equal to the time duration of the negative portion, and for the last cycle, the time duration of the second portion is such that the energy of the second portion is substantially equal to the summation of the energy differences between the positive and negative portions of each preceding cycle and the energy of the first portion of the last cycle.

In a third aspect, the invention is related to an apparatus for applying a high-energy, high-frequency pulse of energy across a heart for restoring effective cardiac rhythm. The apparatus includes a capacitor having a first terminal and a second terminal, a battery for charging the capacitor to an initial voltage level sufficient to shock the heart, a first electrode for contacting a first cardiac-tissue contact point and a second electrode for contacting a second cardiac-tissue contact point. Both the first and second electrodes are responsive to one of either the first or second terminals of the capacitor. The apparatus further includes a switching circuit for connecting the first electrode to the first terminal of the capacitor and the second electrode to the second terminal of the capacitor and periodically interchanging the connections, and a controller for controlling the switching circuit during discharge of the capacitor to produce a waveform comprising a plurality of cycles each having a positive portion and a negative portion, the waveform substantially lacking a dc component.

In a fourth facet, the invention pertains to an apparatus for applying a high-energy, high-frequency pulse across a heart for restoring effective cardiac rhythm. The apparatus includes a waveform generator for producing a high-frequency cyclic waveform comprising a plurality of waveform cycles and a controller responsive to the cyclic waveform for outputting a high-energy pulse comprising a plurality of substantially complete waveform cycles, at least one waveform cycle having a peak-to-peak voltage sufficient to shock the heart. The apparatus further includes a first electrode for contacting a first cardiac-tissue contact point, the first electrode responsive to the controller and a second electrode for contacting a second cardiac-tissue contact point, the second electrode responsive to a substantially constant potential.

In a detailed aspect of the apparatus, the cyclic waveform is a symmetric waveform, i.e., sine wave, square wave, etc. In another aspect, the at least one waveform has a peak-to-peak voltage of between approximately 1000 volts to 1200 volts. In yet another facet, the frequency of the cyclic waveform is between approximately 10 kHz and 500 kHz. In another aspect, the controller controls the total energy delivered to the tissue by varying the peak-to-peak voltage of the cyclic waveform and/or by varying the time duration of the pulse.

These and other aspects and advantages of the invention will become apparent from the following detailed description and the accompanying drawings, which illustrate by way of example the features of the invention.

DETAILED DESCRIPTION OF PREFERRED EMBODIMENTS

Figure 3:
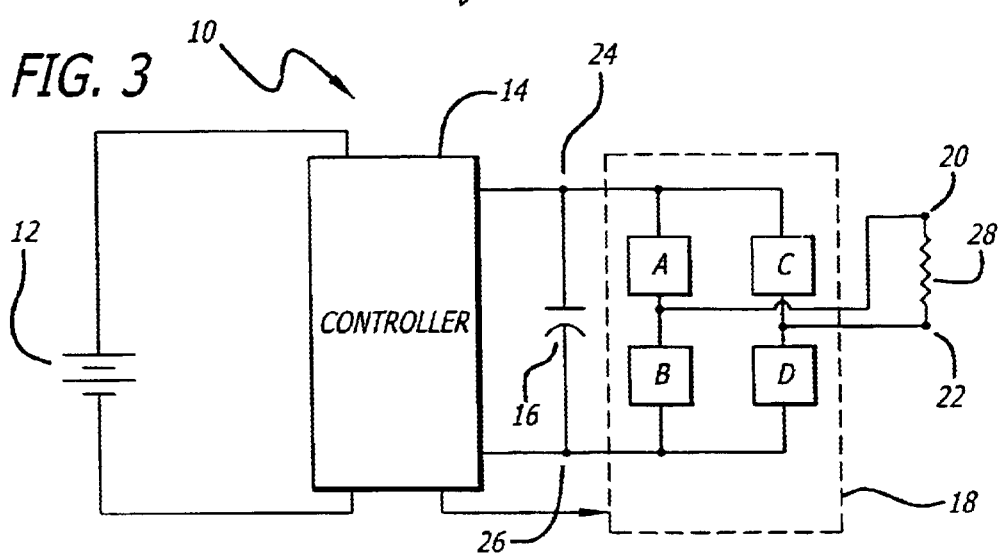
FIG. 3 is a schematic block diagram of one embodiment of a defibrillator system for producing a high-energy, high-frequency, capacitor-discharge-waveform pulse.

Turning now to the drawings, in which like reference numerals are used to designate like or corresponding elements among the several figures, in FIG. 3 there is shown a defibrillator system 10. The defibrillator system 10 includes a battery 12, a programmable controller 14, a capacitor 16, a commutating or switching circuit 18, a first electrode 20 and a second electrode 22. The switching circuit 18 is used to interchange the potentials at the first terminal 24 and second terminal 26 of the capacitor 16 during discharge, such that, for a first period of time, the first electrode 20 is responsive to the first terminal 24 of the capacitor while the second electrode is responsive to the second terminal 26 and during a second period of time the first electrode is responsive to the second terminal 24 of the capacitor and the second electrode 22 is responsive to the first terminal 24.

Figure 4A:
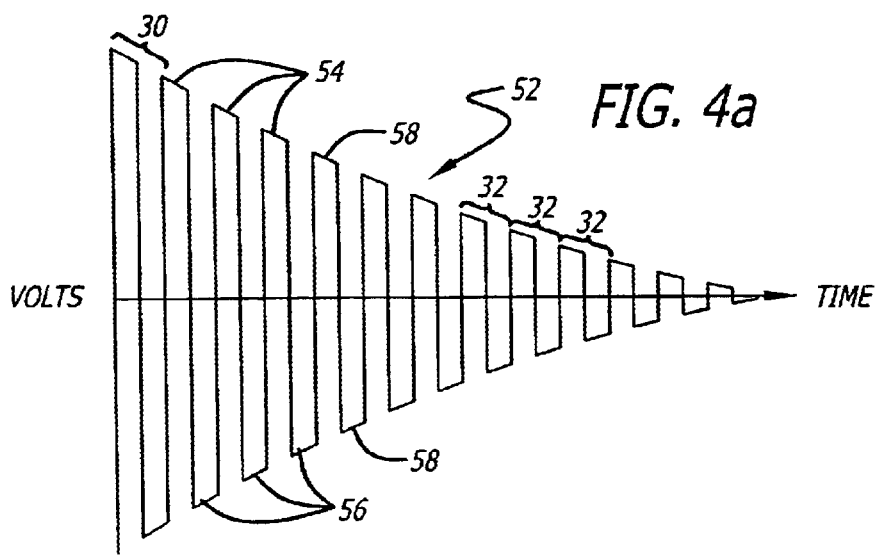
FIGS. 4a through 4c depict various forms of high-energy, high-frequency, capacitor-discharge-waveform pulses used to counter shock the heart in accordance with the invention.

The switching circuit may be of any configuration suitable for interchanging the terminals 24, 26 and electrodes 20, 22 as just described. In the embodiment shown in FIG. 3, the switching circuit includes four switches A, B, C and D which operate in pairs A–D and B–C. For one period of time, switches A and D are closed while switches B and C are open. Thus during this period of time, the first terminal 24 of the capacitor is connected to the first electrode 20 and the second terminal 26 is connected to the second electrode 22. For a subsequent period of time, switches B and C are closed while switches A and D are open. Thus during this period of time, the first terminal 24 of the capacitor is connected to the second electrode 22 and the second terminal 26 is connected to the first electrode 20. In the diagram of FIG. 3, the switches may be IRFPG50 FET switches. The controller may be a 80C51 microprocessor controller In operation, the battery 12 charges the capacitor 16 to a desired voltage level depending on the type of defibrillator system, as described further below. The desired voltage level is maintained by the controller 14. The electrodes 20, 22 are positioned across the heart 28 and the capacitor 16 is discharged through the electrodes. Under control by the controller 14, the switching circuit 18 interchanges the terminals 24, 26 and electrodes 20, 22 at a sufficiently high frequency. As shown in FIG. 4a, the switching action of the defibrillator produces a pulse 52 having alternating positive portions 54 and negative portions 56 forming a waveform with a capacitor discharge curve profile. Because the portions 54, 56 are produced by a discharging capacitor, the peak 58 of each positive and negative portion is slanted. This type of waveform is referred to herein as a "slanted square wave."

Figure 1:
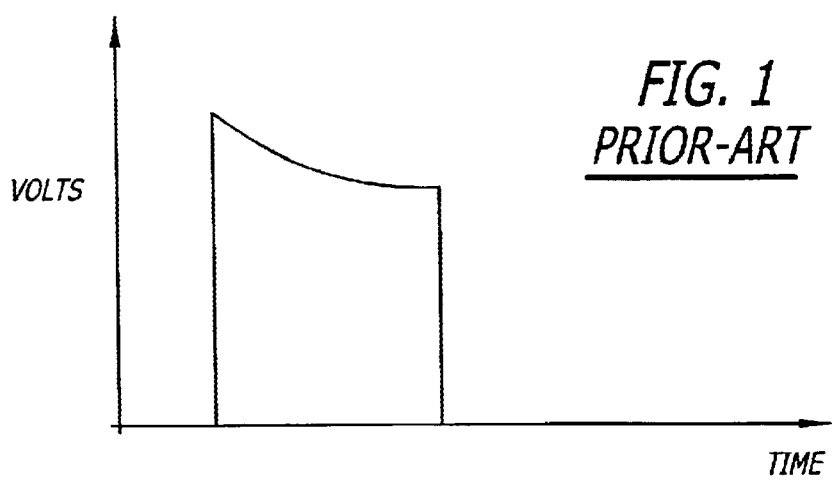
FIG. 1 depicts a monophasic trapezoidal truncated pulse used to counter shock a heart.
Figure 2:
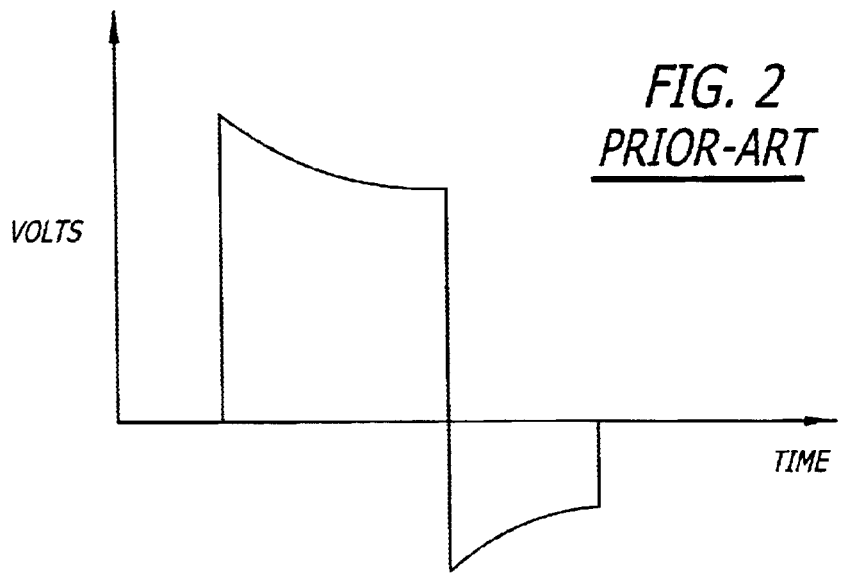
FIG. 2 depicts a biphasic trapezoidal truncated pulse used to counter shock a heart.

The switching circuit 18 (FIG. 3) operates at a high frequency to produce a slanted square wave. Any high-energy pulse at a frequency fast enough to stimulate the heart may be used. For example, frequencies in the 10 kHz to 500 kHz range have been found to stimulate the heart to correct arrhythmias or defibrillation. During capacitor 16 discharge, the waveform (FIG. 4a) alternates between positive and negative voltages at a sufficiently high frequency such that the waveform is symmetric like and the net dc component of the pulse 52 is substantially zero. Accordingly, the defibrillator essentially lacks the dc component typically produced by a discharging capacitor as used in prior art defibrillators as shown in FIGS. 1 and 2. Thus the patient undergoing defibrillation is not exposed to dc current and thus does not experience the high level of pain typically associated with prior art defibrillation methods.

Figure 4B:
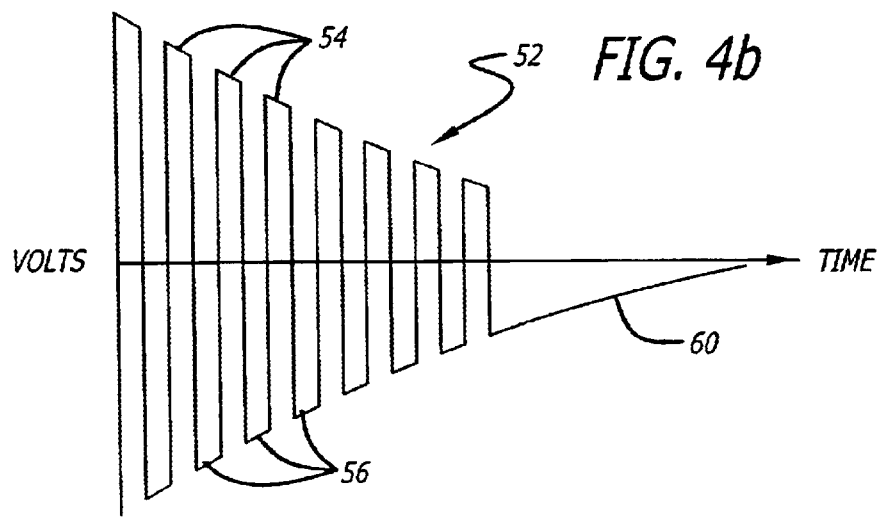

A substantially net dc component of zero may be obtained in any of several ways. In one configuration of the defibrillator, the controller switches between positive and negative voltages to produce the waveform shown in FIG. 4b. This waveform comprises an equal number of positive portions 54 and negative portions 56 with the capacitor completely discharging during a last negative portion 60. Taking the area under each positive and negative portion to be equal to the energy provided by that portion, the controller determines, a priori, based on the capacitor characteristics, e.g., size, discharge curve, etc., initial charge and the controller switching frequency, an appropriate point in time at which the last negative portion 60 occurs such that the summation of the positive and negative energies within the pulse 52 is substantially equal to zero.

Figure 4C:
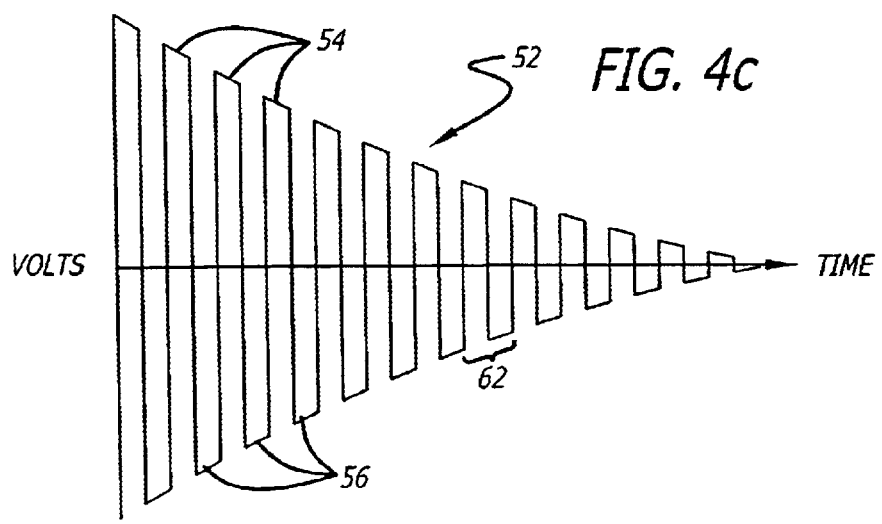

In another configuration, the controller switches between positive and negative voltages to produce the waveform shown in FIG. 4c. This waveform also comprises an equal number of positive portions 54 and negative portions 56. The controller, however, adjusts the width of each negative portion 56 such that it is larger than the width of its preceding positive portion 54. Thus, the net energy under each pair of positive and negative portions is substantially zero. The waveform ends on a complete cycle 62, i. e., one positive portion and one negative portion, such that the cumulative energy provided within the pulse 52 is substantially zero.

The defibrillator system 10 may be configured as an external device or an internal device. For an external device, the total amount of energy applied to the heart 28 is typically between 200–400 joules. In such a device, a battery may, through a dc-to-dc step-up converter, be used to fully charge a 32 $\mu$F capacitor up to about 5000 volts. With reference to FIG. 4a, during discharge, the peak-to peak voltage of the initial cycle 30 of the waveform is approximately 10,000 volts. The waveform alternates between positive and negative portions at a frequency of 10 k to 500 kHz range. For subsequent cycles 32, the peak-to-peak voltage progressively decreases until the capacitor 16 is fully discharged.

For an internal device, the total amount of energy applied to the heart 28 is typically between 40–80 joules. In such a device, a battery may, through a dc-to-dc step-up converter, be used to fully charge a 250 $\mu$F capacitor up to about 300 to 800 volts. Thus, during discharge, the peak-to peak voltage of the initial cycle 30 of the waveform is approximately 1600 volts. As with the external device, the waveform alternates between positive and negative portions at a frequency of 10 k to 500 kHz, and for subsequent cycles 32, the peak-to-peak voltage progressively decreases until the capacitor 16 is fully discharged.

For both the external and internal devices, the total amount of energy delivered to the heart may be controlled in any of several ways. For example, the capacitor may be charged to a level less than its full capacity, thereby reducing the initial peak-to-peak voltage 30. Alternatively, the time duration of the pulse may be controlled by setting all switches A, B, C and D open, so as to truncate the pulse prior to full discharge of the capacitor 16. Thus, various combinations of pulse amplitude and pulse duration provide for control over the amount of energy delivered to the heart.

Figure 5:
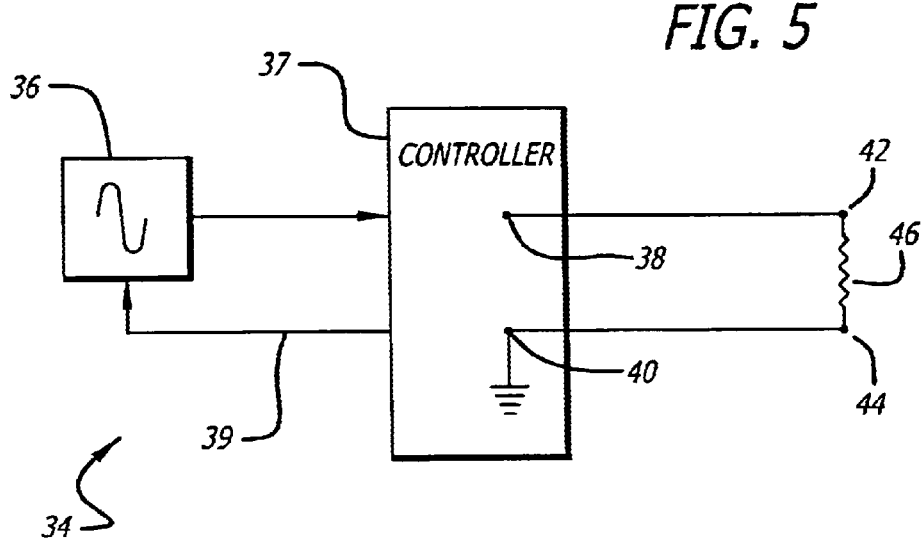
FIG. 5 is a schematic block diagram of another embodiment of a defibrillator system for producing a high-energy, high-frequency, symmetric-waveform pulse.

In another embodiment of the invention, as shown in FIG. 5, an external defibrillator system 34 includes a symmetric waveform generator 36 and a controller 37. The controller 37 provides control signals 39 to the waveform generator 36 that select the type, e.g., sine wave, and frequency, e.g., 10 kHz to 500 kHz, of the generator output waveform. The waveform generator 36 outputs the waveform to the controller 37, which in turn, filters the waveform and step-up transforms the peak-to-peak voltage of the waveform to a level sufficient to shock the heart, such as between 1200 to 1600 volts. The controller 37 also controls the waveform such that it is output through the controller output 38 as a pulse having a duration of between 10 milliseconds and 20 milliseconds. The controller 37 further controls the waveform pulse such that the pulse comprises a plurality of complete cycles of the waveform. This ensures that current flow through the heart is substantially symmetrical, i.e., the waveform is on both the positive and negative side of zero for substantially equal amounts of time. The controller also includes a second output 40 for providing a fixed reference potential, such as a return. The defibrillator system 34 also includes a first electrode 42 that is responsive to the first output 38 and a second electrode 44 that is responsive to the second output 40.

In operation, the first electrode 42 and second electrode 44 are placed across the heart 46 and a symmetric waveform pulse is provided at the first output 38. Current flow through the heart 46 occurs between the first and second electrodes 42, 44. The pulse may be of any form, such as a sine wave, a square wave, or triangle wave. Like the first embodiment of the invention, the pulse is of a sufficiently high frequency to stimulate the heart and the total amount of energy delivered to the heart may be controlled by adjusting the peak-to-peak voltage of the pulse and the duration of the pulse.

Figure 6A:
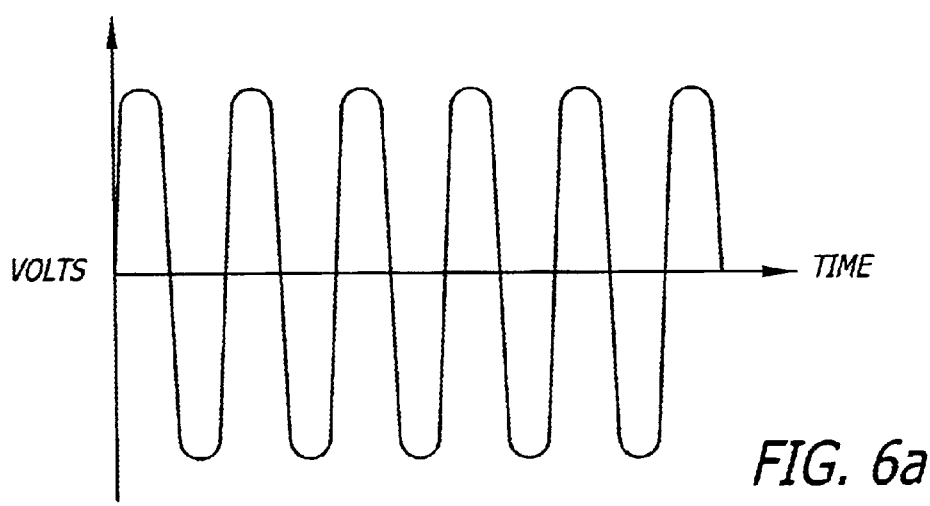
FIGS. 6a and 6b depict various forms of high-energy, high-frequency, symmetric-waveform pulses used to counter shock the heart in accordance with the invention.
Figure 6B:
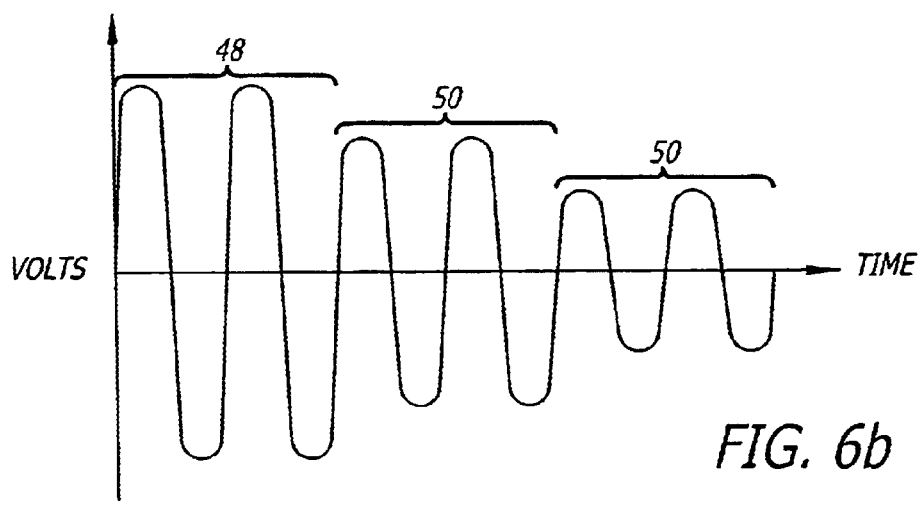

The waveform generator 36 may produce various high-energy, high-frequency pulses comprising symmetric waveforms. As shown in FIG. 6a, the pulse may be a sine wave with a constant peak-to-peak voltage. Another possible pulse, as shown in FIG. 6b, includes a first cycle group 48 having a first peak-to-peak voltage sufficient to shock the heart followed by one or more subsequent cycle groups 50 having different peak-to-peak voltages which may or may not be at a level sufficient to shock the heart. Each cycle group includes at least one complete cycle of the waveform and, to maintain symmetrical current flow through the heart, ends on a complete cycle of the waveform.

By applying a high-energy, high-frequency symmetric waveform to the heart, direct stimulation of the heart by a dc waveform is eliminated and the defibrillation procedure is less painful for the patient. Instead, it has been observed that the high-energy, high-frequency symmetric waveform momentarily disrupts the conduction of electricity through the heart and allows the heart to reset using its own natural pacemaker.

Thus there has been shown and described a new and useful defibrillator system that effectively shocks the heart to correct cardiac arrhythmia or fibrillation in a manner that substantially eliminates the application of pain inducing dc current through the heart.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. For a heart in fibrillation, a method of defibrillating the heart comprising the steps of:

applying, across the heart, a pulse having a time duration and comprising a high-frequency cyclic waveform having a plurality of cycle groups, each group having a positive portion and a negative portion, the waveform having, during the first cycle group, an initial peak-to-peak voltage sufficient to shock the heart and, during each subsequent cycle group, a subsequent peak-to-peak voltage, wherein the cumulative energy of the positive portions within the pulse is substantially equal to the cumulative energy of the negative portions within the pulse; and controlling the total energy delivered to the heart.

2. The method of claim 1 wherein each cycle group comprises at least one cycle of the cyclic waveform.

3. The method of claim 1 wherein each cycle group has a peak-to-peak voltage less than that of the previous cycle group.

4. The method of claim 3 wherein the profile of the cyclic waveform resembles a discharge curve of a capacitor.

5. The method of claim 1 wherein the initial peak-to-peak voltage and each subsequent peak-to-peak voltage are substantially equal.

6. The method of claim 1 wherein the pulse is applied external to the heart and the initial peak-to-peak voltage is between approximately 9000 volts and 10,000 volts.

7. The method of claim 1 wherein the pulse is applied internal to the heart and the initial peak-to-peak voltage is between approximately 1000 volts and 1200 volts.

8. The method of claim 1 wherein the cyclic waveform has a frequency of between approximately 10 kHz and 500 kHz.

9. The method of claim 1 wherein the lime duration of the pulse is between approximately 10 milliseconds and 20 milliseconds.

10. The method of claim 1 wherein the total energy is controlled by varying the initial and subsequent peak-to-peak voltages.

11. The method of claim 1 wherein the total energy is controlled by varying the time duration of the pulse.

12. A method of applying a high-energy, high-frequency pulse across a heart for restoring effective cardiac rhythm, said method comprising the steps of:

charging a capacitor to an initial voltage level sufficient to shock the heart, the capacitor having a first terminal and a second terminal;

applying the potential at the first terminal of the capacitor to a first cardiac-tissue contact point;

applying the potential at the second terminal of the capacitor to a second cardiac-tissue contact point;

initiating the discharge of the capacitor; and periodically interchanging the potentials at the first and second terminals of the capacitor during discharge of the capacitor to produce a waveform comprising a plurality of cycles each having a positive portion and a negative portion, wherein the potentials are interchanged such that the cumulative energy of the positive portions is substantially equal to the cumulative energy of the negative portions.

13. The method of claim 12 wherein the potentials are interchanged at fixed time intervals such that the cycles have positive and negative portions of substantially equal time duration.

14. The method of claim 13 wherein the potentials are interchanged until the capacitor is completely discharged.

15. The method of claim 12 wherein the potentials are interchanged such that, for each cycle, the energy in the positive portion is substantially equal to the energy in the negative portion.

16. The method of claim 15 wherein the time duration of one portion of each cycle is greater than the time duration of the other portion of the same cycle.

17. The method of claim 12 wherein:

for each cycle, except the last, the potentials are interchanged such that the time duration of the positive portion is substantially equal to the time duration of the negative portion; and for the last cycle, the time duration of the negative portion is such that the energy of the negative portion is substantially equal to the summation of the energy differences between the positive and negative portions of each preceding cycle and the energy of the positive portion of the last cycle.

18. The method of claim 12 further comprising the step of controlling the total energy delivered to the heart.

19. The method of claim 18 wherein the total energy is controlled by varying the initial voltage charge across the capacitor.

20. The method of claim 18 wherein the total energy is controlled by varying the time duration of discharge.

21. The method of claim 12 wherein the capacitor is charged to a voltage level between 500 and 600 volts.

22. The method of claim 12 wherein the potentials are interchanged at a frequency in the range of approximately 10 kHz to 500 kHz.

23. An apparatus for applying a high-energy, high-frequency pulse of energy across a heart for restoring effective cardiac rhythm, said apparatus comprising:

a capacitor having a first terminal and a second terminal;

a battery for charging the capacitor to an initial voltage level sufficient to shock the heart;

a first electrode for contacting a first cardiac-tissue contact point, the first electrode responsive to one of either the first or second terminals of the capacitor;

a second electrode for contacting a second cardiac-tissue contact point, the second electrode responsive to one of either the first or second terminals of the capacitor;

a switching circuit for connecting the first electrode to the first terminal of the capacitor and the second electrode to the second terminal of the capacitor and periodically interchanging the connections; and a controller for controlling the switching circuit during discharge of the capacitor to produce a waveform comprising a plurality of cycles each having a positive portion and a negative portion, wherein the connections are interchanged such that the cumulative energy of the positive portions is substantially equal to the cumulative energy of the negative portions.

24. The apparatus of claim 23 wherein the controller interchanges the connections at fixed time intervals such that the cycles have positive and negative portions of substantially equal time duration.

25. The apparatus of claim 24 wherein the connections are interchanged until the capacitor is completely discharged.

26. The apparatus of claim 23 wherein the connections are interchanged such that, for each cycle, the energy in the positive portion is substantially equal to the energy in the negative portion.

27. The apparatus of claim 26 wherein the time duration of one portion of each cycle is greater than the time duration of the other portion of the same cycle.

28. The apparatus of claim 23 wherein:

for each cycle, except the last, the connections are interchanged such that the time duration of the positive portion is substantially equal to the time duration of the negative portion; and for the last cycle, the time duration of the negative portion is such that the energy of the negative portion is substantially equal to the summation of the energy differences between the positive and negative portions of each preceding cycle and the energy of the positive portion of the last cycle.

29. The apparatus of claim 23 wherein the controller controls the total energy delivered to the tissue.

30. The apparatus of claim 29 wherein the total energy is controlled by varying the initial voltage charge across the capacitor.

31. The apparatus of claim 29 wherein the total energy is controlled by varying the time duration of discharge.

32. An apparatus for applying a high-energy, high-frequency pulse across a heart for restoring effective cardiac rhythm, said apparatus comprising:

a waveform generator for producing a high-frequency cyclic waveform comprising a plurality of waveform cycles, each cycle having a positive portion and a negative portion;

a controller responsive to the cyclic waveform for outputting a high-energy pulse comprising a plurality of substantially complete waveform cycles such that the pulse has an equal number of positive portions and negative portions, at least one waveform cycle having a peak-to-peak voltage sufficient to shock the heart;

a first electrode for contacting a first cardiac-tissue contact point, the first electrode responsive to the controller; and a second electrode for contacting a second cardiac-tissue contact point, the second electrode responsive to a substantially constant potential.

33. The apparatus of claim 32 wherein the cyclic waveform is a symmetric waveform.

34. The apparatus of claim 32 wherein the at least one waveform has a peak-co-peak voltage of between approximately 1000 volts to 1200 volts.

35. The apparatus of claim 32 wherein the frequency of the cyclic waveform is between approximately 10 kHz and 500 kHz.

36. The apparatus of claim 32 wherein the second electrode is responsive to a return potential.

37. The apparatus of claim 32 wherein the controller controls the total energy delivered to the tissue.

38. The apparatus of claim 37 wherein the total energy is controlled by varying the peak-to-peak voltage of the cyclic waveform.

39. The apparatus of claim 37 wherein the total energy is controlled by varying the time duration of the pulse.

* * * * *